(12) United States Patent
Wadsworth et al.

(10) Patent No.: US 6,737,089 B2
(45) Date of Patent: May 18, 2004

(54) MORINDA CITRIFOLIA (NONI) ENHANCED ANIMAL FOOD PRODUCT

(75) Inventors: John J. Wadsworth, Orem, UT (US); Stephen P. Story, Alpine, UT (US); Claude Jarkae Jensen, Cedar Hills, UT (US)

(73) Assignee: Morinda, Inc., Orem, UT (US)

( * ) Notice: Subject to any disclaimer, the term of this patent is extended or adjusted under 35 U.S.C. 154(b) by 0 days.

(21) Appl. No.: 09/836,881

(22) Filed: Apr. 17, 2001

(65) Prior Publication Data

US 2002/0182276 A1 Dec. 5, 2002

Related U.S. Application Data

(63) Continuation-in-part of application No. 09/829,039, filed on Apr. 9, 2001, now Pat. No. 6,528,106, which is a continuation of application No. 09/384,784, filed on Aug. 27, 1999, now Pat. No. 6,254,913.

(51) Int. Cl.[7] .......................... A61K 35/78; A23K 1/00
(52) U.S. Cl. ..................... 424/777; 424/765; 424/442; 426/2; 426/53; 426/615; 426/489; 426/495
(58) Field of Search ................................ 424/442, 725, 424/777, 765; 426/2, 53, 599, 615, 489, 495

(56) References Cited

U.S. PATENT DOCUMENTS

| | | | |
|---|---|---|---|
| 5,288,491 A | * | 2/1994 | Moniz |
| 5,431,927 A | | 7/1995 | Hand et al. ............... 426/2 |
| 5,616,569 A | | 4/1997 | Reinhart ................... 514/54 |
| 5,770,217 A | * | 6/1998 | Kutilek, III et al. |
| 5,851,573 A | | 12/1998 | Lepine et al. ............. 426/74 |
| 5,962,043 A | | 10/1999 | Jones et al. ............... 426/2 |
| 5,976,549 A | * | 11/1999 | Lewandowski |
| 6,039,952 A | | 3/2000 | Sunvold et al. .......... 424/195.1 |
| 6,133,323 A | | 10/2000 | Hayek ...................... 514/725 |
| 6,156,355 A | | 12/2000 | Shields, Jr. et al. ..... 426/74 |
| 6,214,351 B1 | * | 4/2001 | Wadsworth et al. |
| 6,299,925 B1 | * | 10/2001 | Xiong et al. |
| 6,405,948 B1 | * | 6/2002 | Hahn et al. |
| 6,436,449 B2 | * | 8/2002 | Gidlund |
| 2001/0033871 A1 | * | 10/2001 | Gidlund |

FOREIGN PATENT DOCUMENTS

FR 2783137 * 3/2000

OTHER PUBLICATIONS

Product Alert. Jun. 12, 2000. Vol 30, No. 11, PROMT Abstract.*
Product Alert. Dec. 27, 1999. Vol 29, No. 24, PROMT Abstract.*
Product Alert. Oct. 11, 1999. Vol 29, No. 19, PROMT Abstract.*
Product Alert. Jul. 27, 1998. PROMT Abstract.*
Julia F. Morton, "The Ocean–Going Noni, or Indian Mulberry (*Morinda Citrifolia, Rubiaceae*) and Some of Its Colorful" Relatives, Economic Botany, vol. 46, No. 3, 1992, pp. 241–256.

* cited by examiner

*Primary Examiner*—Christopher R. Tate
(74) *Attorney, Agent, or Firm*—Kirton & McConkie; Michael F. Krieger

(57) ABSTRACT

The present invention advances prior art animal food products by providing an animal food product formulated with *Morinda Citrifolia*, or Noni, from the Indian Mulberry plant. The addition of Noni to the animal food product of the present invention serves to provide significant health advantages not found in prior art animal food products.

35 Claims, No Drawings

MORINDA CITRIFOLIA (NONI) ENHANCED ANIMAL FOOD PRODUCT

RELATED APPLICATIONS

This application is a continuation-in-part application and claims priority to U.S. patent application Ser. No. 09/829,039 filed Apr. 9, 2001, entitled MORINDA CITRIFOLIA DIETARY FIBER, now issued as U.S. Pat. No. 6,528,106, which is a continuation of U.S. patent application Ser. No. 09/384,784 filed Aug. 27, 1999, entitled MORINDA CITRIFOLIA DIETARY FIBER, now issued as U.S. Pat. No. 6,254,913.

BACKGROUND

1. Field of the Invention

The field of the invention relates to animal food products, and particularly to animal food products for domestic and companion animals. Specifically, the present invention relates to an improved animal food product and composition enhanced with *Morinda citrifolia* or Tahitian Noni dietary fiber.

2. Background

Animal Food Products

Animal food products designed for domestic animals, livestock, or pets, but particularly companion animals, such as dogs and cats, are generally and preferably prepared as full-feeding foods, which means that the particular composition contains all the necessary nutrients and supplements needed to maintain the health and vigor of the pet. The food composition is balanced in nutrition so that a diet limited to that particular feed will fulfill all of the pet's nutritional needs. Such food products are achievable in two ways. First, industry guidelines, as set and monitored by the Association of American Feed Control Officials (AAFCO), are provided in order to ensure a proper balance of nutrients; and second, each animal food product is actually tested in its specific formulations in appropriate feeding studies.

The typical ingredients contained within a pet food formulation are protein, carbohydrates, fat, vitamins and minerals. Each of these is present in varying percentages by weight of the specific formulation or composition, sufficient to meet the complete nutritional requirements of the pet. In addition, other ingredients may be added depending upon the specific needs of the animal for which the food is intended.

A wide variety of different animal food formulations are commercially available. Most include either wet or dry type products. The definition of wet or dry is derived from the percentage of water existing in the formulation by weight. Typically, such animal food formulations are designed to be consumed by any breed. In the past, the nutrients or ingredients in these formulations are not typically designed to provide specific advantages to a pet if desired or needed. Recently however, animal food formulations have been designed with a specific goal in mind. Many animal food formulations available on the market today are specialized in that they may cater to animals of different ages, different breeds, or those with certain needs, such as obesity, bone loss, etc. Other formulations address different energy requirements among animals. An additional segment of the animal food market incorporates differences in ingredient usage or product form, which tend to lend themselves to more attractive tastes or varieties.

*Morinda citrifolia*

The Indian Mulberry plant, known scientifically as *Morinda citrifolia* L., is a shrub, or small or medium-sized tree 3 to 10 meters high. It grows in tropical coastal regions around the world. The plant grows randomly in the wild, and is also cultivated in plantations and small individual growing plots. *Morinda citrifolia* has somewhat rounded branches and evergreen, opposite (or spuriously alternate), dark, glossy, wavy, prominently-veined leaves. The leaves are broadly elliptic to oblong, pointed at both ends, 10–30 cm in length and 5–15 cm wide.

*Morinda citrifolia* flowers are small, white, 3 to 5 lobed, tubular, fragrant, and about 1.25 cm long. The flowers develop into compound fruits composed of many small drupes fused into an ovoid, ellipsoid or roundish, lumpy body, 5–10 cm long, 5–7 cm thick, with waxy, white or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged, 2-celled stones, each containing about 4 seeds.

When fully ripe, the fruit has a pronounced odor like rancid cheese. Although the fruit has been eaten by several nationalities as food, the most common use of the Indian mulberry plant was as a red and yellow dye source. Recently, there has been an interest in the nutritional and health benefits of the Indian mulberry plant.

*Morinda citrifolia* has been discovered to contain health enhancing enzymes that aid in easing inflammation, calming feelings of anxiety, supporting weight management, and promoting circulatory health in humans. Moreover, *Morinda citrifolia* is considered to be an adaptogenic herb, a herb which supports balanced body systems by responding to the body's need for stimulation or relaxation.

SUMMARY AND OBJECTS OF THE INVENTION

The present invention is directed to a method of implementing *Morinda citrifolia*, into various compositions and formulas of animal food products. In one currently preferred embodiment, a quantity of *Morinda citrifolia* fruit juice and pulp is obtained, using the process as described below. Subsequently the resulting fruit juice and dietary fiber is added to an animal food product for providing significant health advantages over prior art animal food products.

The *Morinda citrifolia* fruit juice is obtained from the puree of the fruit of the Indian Mulberry plant and is further processed into fruit juice, wherein it may be added or mixed with other ingredients.

To produce the dietary fiber, the wet pulp is filtered from the juice, wherein the wet pulp has a fiber content of from about 10 to 40 percent, by weight. The wet pulp is preferably pasteurized at a temperature of at least 181° F. (83° C.). The wet pulp can be dried or used wet. Drying is preferably accomplished using conventional drying techniques, such as freeze drying, drum drying, tray drying, sun drying, and spray drying. The dried *Morinda citrifolia* pulp preferably has a moisture content in the range from 0.1 to 15 percent by weight and a fiber content in the range from 0.1 to 30 percent by weight.

The *Morinda citrifolia* pulp can be further processed into a high fiber dietary product containing additional ingredients, such as a supplemental dietary fiber, a sweetener, a flavoring agent, coloring agent, and/or a nutritional ingredient.

In another embodiment, a quantity of *Morinda citrifolia* juice and pulp is obtained and pasteurized or enzymatically treated. The juice and pulp mixture is then dried to a moisture content less than about 20%, by weight. The dried juice and pulp contains protein from the *Morinda citrifolia* plant at a concentration typically from 0.1 to 15 percent by weight, and fiber at a concentration from 0.1 to 20 percent by weight. Additional ingredients are preferably mixed to the dried juice and pulp, such as a supplemental nutritional ingredient with the juice and pulp.

Therefore, it is an object of the preferred embodiments of the present invention to provide an animal food product comprising *Morinda Citrifolia*.

It is another object of the preferred embodiments of the present invention to provide an animal food product having significant health benefits.

To achieve the foregoing objects, and in accordance with the invention as embodied and broadly described herein, the present invention features an animal food product comprising protein, fats, vitamins, minerals, water, and carbohydrates, wherein the carbohydrates comprise *Morinda citrifolia* present in an amount by weight from about 3 to 7 percent of the total dietary fiber contained within the animal food product.

The present invention also features a process for enhancing the health and vigor of an animal comprising the step of feeding the animal a diet of an animal food product containing an effective amount of *Morinda citrifolia* dietary fiber comprising 3 to 7 percent by weight of the total dietary fiber composition contained therein.

DETAILED DESCRIPTION OF THE PREFERRED EMBODIMENTS

It will be readily understood that the components of the present invention, as generally described, could be arranged and designed in a wide variety of different configurations. Thus, the following more detailed description of the embodiments of the system and method of the present is not intended to limit the scope of the invention, as claimed, but is merely representative of the presently preferred embodiments of the invention.

I. General Discussion of *Morinda citrifolia* Dietary Fiber

The present invention is directed to fruit juice and dietary fiber from the Indian mulberry (*Morinda citrifolia*), or Noni, plant. The fiber is obtained as a byproduct of the production of *Morinda citrifolia* juice. The specific methods and procedures used to obtain the *Morinda citrifolia* dietary fiber may be found in co-pending U.S. patent application Ser. No. 09/829,039 filed Apr. 9, 2001 entitled "*Morinda citrifolia* Dietary Fiber" or in co-pending U.S. patent application Ser. No. 09/384,784 filed Aug. 27, 1999 entitled "*Morinda citrifolia* Dietary Fiber," each of which are incorporated by reference herein.

In a currently preferred process of producing *Morinda citrifolia* juice, the fruit is either hand picked or picked by mechanical equipment. The fruit can be harvested when it is at least one inch (2–3 cm) and up to 12 inches (24–36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, with most fruit being held from 2 to 3 days. The fruit is ripened or aged by being placed on equipment so it does not contact the ground. It is preferably covered with a cloth or netting material during aging, but can be aged without being covered. When ready for further processing the fruit is light in color, from a light green, light yellow, white or translucent color. The fruit is inspected for spoilage or for excessively green color and hard firmness. Spoiled and hard green fruit is separated from the acceptable fruit.

The ripened and aged fruit is preferably placed in plastic lined containers for further processing and transport. The containers of aged fruit can be held from 0 to 30 days. Most fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into finished juice product. The containers can be stored in refrigerated, frozen, or room temperature conditions. The *Morinda citrifolia* juice and puree are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 181° F. (83° C.) or higher up to 212° F. (100° C.).

The product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp are further processed by separating the pulp from the juice through filtering equipment. The filtering equipment preferably consists of, but is not limited to, a centrifuge decanter, a screen filter with a size from 1 micron up to 2000 microns, more preferably less than 500 microns, a filter press, reverse osmosis filtration., and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The wet pulp typically has a fiber content of 10 to 40 percent by weight. The wet pulp is preferably pasteurized at a temperature of 181° F. (83° C.) minimum and then packed in drums for further processing or made into a high fiber product.

The wet pulp may be further processed by drying. The methods of drying consist of but are not limited to freeze drying, drum drying, tray drying, sun drying, and spray drying. The dried *Morinda citrifolia* pulp preferably has a moisture content in the range from 0.1 to 15 percent by weight and more preferably from 5 to 10 percent by weight. The dried pulp preferably has a fiber content in the range from 0.1 to 30 percent by weight, and more preferably from 5 to 15 percent by weight.

The high fiber product typically includes, but is not limited to, wet or dry *Morinda citrifolia* pulp, supplemental fiber ingredients, water, sweeteners, flavoring agents, coloring agents, and nutritional ingredients. The supplemental fiber ingredients can include, but are not limited to plant based fiber products, either commercially available or developed privately. Examples of some typical fiber products are guar gum, gum arabic, soy bean fiber, oat fiber, pea fiber, fig fiber, citrus pulp sacs, hydroxymethylcellulose, cellulose, seaweed, food grade lumber or wood pulp, hemicellulose, etc. Other supplemental fiber ingredients may be derived from grains or grain products. The concentrations of these other fiber raw materials typically range from 0 up to 30 percent, by weight, and more preferably from 10 to 30 percent by weight.

Typical sweeteners typically include, but are not limited to, natural sugars derived from corn, sugar beet, sugar cane, potato, tapioca, or other starch-containing sources that can be chemically or enzymatically converted to crystalline chunks, powders, and/or syrups. Also sweeteners can consist of artificial or high intensity sweeteners, some of which are aspartame, sucralose, stevia, saccharin, etc. The concentration of sweeteners is preferably between from 0 to 50 percent by weight, of the formula, and more preferably between about 1 and 5 percent by weight.

Typical flavors can include, but are not limited to, artificial and/or natural flavor or ingredients that contribute to palatability. The concentration of flavors is preferably from 0 up to 15 percent by weight, of the formula. Colors preferably include, but are not limited to, food grade artificial or natural coloring agents having a concentration ranging from 0 up to 10 percent by weight, of the formula.

Typical nutritional ingredients consist of but are not limited to vitamins, minerals, trace elements, herbs, botanical extracts, bioactive chemicals and compounds at concentrations from 0 up to 10 percent by weight. Examples of vitamins one can add to the fiber composition include, but are not limited to, vitamins A, B1 through B12, C, D, E, Folic Acid, Pantothenic Acid, Biotin, etc. Examples of minerals and trace elements one can add to the fiber composition include, but are not limited to, calcium, chromium, copper, cobalt, boron, magnesium, iron, selenium, manganese, molybdenum, potassium, iodine, zinc, phosphorus, etc. Herbs and botanical extracts include, but are not limited to, alfalfa grass, bee pollen, chlorella powder, Dong Quai powder, Ecchinacea root, Gingko Biloba extract, Horsetail herb, Indian mulberry, Shitake mushroom, spirulina seaweed, grape seed extract, etc. Typical bioactive chemicals can include, but are not limited to, caffeine, ephedrine, L-carnitine, creatine, lycopene, etc.

The juice and pulp can be dried using a variety of methods. The juice and pulp mixture can be pasteurized or enzymatically treated prior to drying. The enzymatic process begins with heating the product to a temperature between 75° F. and 135° F. It is then treated with either a single enzyme or a combination of enzymes. These enzymes include, but are not limited to, amylase, lipase, protease, cellulase, bromelin, etc. The juice and pulp can also be dried with other ingredients, such as those described above in connection with the high fiber product. The typical nutritional profile of the dried juice and pulp is 1 to 20 percent moisture, 0.1 to 15 percent protein, 0.1 to 20 percent fiber, and the vitamin and mineral content.

The filtered juice and the water from washing the wet pulp are preferably mixed together. The filtered juice is preferably vacuum evaporated to a brix of 40 to 70 and a moisture of 0.1 to 80 percent, more preferably from 25 to 75 percent. The resulting concentrated *Morinda citrifolia* juice may or may not be pasteurized. The juice would not be pasteurized in circumstances where the sugar content or water activity was sufficiently low enough to prevent microbial growth. It is packaged for storage, transport and/or further processing.

The Indian Mulberry plant is rich in natural ingredients. Those ingredients that have been discovered include: from the leaves: alanine, anthraquinones, arginine, ascorbic acid, aspartic acid, calcium, beta-carotene, cysteine, cystine, glycine, glutamic acid, glycosides, histidine, iron, leucine, isoleucine, methionine, niacin, phenylalanine, phosphorus, proline, resins, riboflavin, serine, beta-sitosterol, thiamine, threonine, tryptophan, tyrosine, ursolic acid, and valine; from the flowers: acacetin-7-o-beta-d(+)-glucopyranoside, 5,7-dimethyl-apigenin-4'-o-beta-d(+)-galactopyranoside, and 6,8-dimethoxy-3-methylanthraquinone-1-o-beta-rhamnosyl-glucopyranoside; from the fruit: acetic acid, asperuloside, butanoic acid, benzoic acid, benzyl alcohol, 1-butanol, caprylic acid, decanoic acid, (E)-6-dodeceno-gamma-lactone, (Z,Z,Z)-8,11,14-eicosatrienoic acid, elaidic acid, ethyl decanoate, ethyl hexanoate, ethyl octanoate, ethyl palmitate, (Z)-6-(ethylthiomethyl) benzene, eugenol, glucose, heptanoic acid, 2-heptanone, hexanal, hexanamide, hexanedioic acid, hexanoic acid (hexoic acid), 1-hexanol, 3-hydroxy-2-butanone, lauric acid, limonene, linoleic acid, 2-methylbutanoic acid, 3-methyl-2-buten-1-ol, 3-methyl-3-buten-1-ol, methyl decanoate, methyl elaidate, methyl hexanoate, methyl 3-methylthio-propanoate, methyl octanoate, methyl oleate, methyl palmitate, 2-methylpropanoic acid, 3-methylthiopropanoic acid, myristic acid, nonanoic acid, octanoic acid (octoic acid), oleic acid, palmitic acid, potassium, scopoletin, undecanoic acid, (Z,Z)-2,5-undecadien-1-ol, and vomifol; from the roots: anthraquinones, asperuloside (rubichloric acid), damnacanthal, glycosides, morindadiol, morindine, morindone, mucilaginous matter, nor-damnacanthal, rubiadin, rubiadin monomethyl ether, resins, soranjidiol, sterols, and trihydroxymethyl anthraquinone-monomethyl ether; from the root bark: alizarin, chlororubin, glycosides (pentose, hexose), morindadiol, morindanigrine, morindine, morindone, resinous matter, rubiadin monomethyl ether, and soranjidiol; from the wood: anthragallol-2,3-dimethylether; from the tissue culture: damnacanthal, lucidin, lucidin-3-primeveroside, and morindone-6beta-primeveroside; from the plant: alizarin, alizarin-alpha-methyl ether, anthraquinones, asperuloside, hexanoic acid, morindadiol, morindone, morindogenin, octanoic acid, and ursolic acid.

Recently, many health benefits have been discovered stemming from the use of products containing *Morinda citrifola*. One benefit of *Morinda citrifola* is found in its ability to isolate and produce Xeronine, a relatively small alkaloid physiologically active within the body. Xeronine occurs in practically all healthy cells of plants, animals and microorganisms. Even though *Morinda citrifola* has a negligible amount of free Xeronine, it contains appreciable amounts of the precursor of Xeronine, called Proxeronine. Further, *Morinda citrifola* contains the inactive form of the enzyme Proxeronase which releases Xeronine from Proxeronine. A paper entitled, "The Pharmacologically Active Ingredient of Noni" by R. M. Heinicke of the University of Hawaii, indicates that Noni is "the best raw material to use for the isolation of Xeronine," because of the building blocks of Proxeronine and Proxeronase. These building blocks aid in the isolation and production of Xeronine within the body. The function of the essential nutrient Xeronine is fourfold.

First, Xeronine serves to activate dormant enzymes found in the small intestines. These enzymes are critical to efficient digestion, calm nerves, and overall physical and emotional energy.

Second, Xeronine protects and keeps the shape and suppleness of protein molecules so that they may be able to pass through the cell walls and be used to form healthy tissue. Without these nutrients going into the cell, the cell can not perform its job efficiently. Without Proxeronine to produce xeronine our cells, and subsequently the body, suffer.

Third, Xeronine assists in enlarging the membrane pores of the cells. This enlargement allows for larger chains of peptides (amino acids or proteins) to be admitted into the cell. If these chains are not used they become waste.

Fourth, Xeronine, which is made from Proxeronine, assists in enlarging the pores to allow better absorption of nutrients.

Each tissue has cells which contain proteins which have receptor sites for the absorption of Xeronine. Certain of these proteins are the inert forms of enzymes which require absorbed Xeronine to become active. Thus Xeronine, by converting the body's procollagenase system into a specific protease, quickly and safely removes the dead tissue from skin. Other proteins become potential receptor sites for hormones after they react with Xeronine. Thus the action of *Morinda citrifola* in making an animal feel well is probably caused by Xeronine converting certain brain receptor proteins into active sites for the absorption of the endorphin, the well being hormones. Other proteins form pores through membranes in the intestines, the blood vessels and other body organs. Absorbing Xeronine on these proteins changes the shape of the pores and thus affects the passage of molecules through the membranes.

Because of its many benefits, *Morinda citrifola* has been known to provide a number of anecdotal effects for cancer, arthritis, headaches, indigestion, malignancies, broken bones, high blood pressure, diabetes, pain, infection, asthma, toothache, blemishes, immune system failure, and others.

II. General Discussion of Animal Food Products

Animal food products, and particularly companion animal foods, are generally classified into three types distinguished by their water content, namely (1) dry pet foods which generally have a water content of less than about 15% by weight, (2) soft and wet pet foods which generally have a water content of 20 to 45% by weight, and (3) pet foods which have a high water content of more than 45% by weight. The animal food products (3) having a high water content are generally sold in canned form. These canned foods require retorting because the high content of water is suitable for growth of microorganisms. Moreover, after can opening, the canned foods should be stored in a refrigerated state because they undergo spoilage very soon. Thus, the foods containing a high water content in canned form require high costs for processing and canning, and are inconvenient to store.

Foods (1) and (2) are easy to pack and transport, and do not need to be refrigerated after unpacking. They are easy to give to animals, and are convenient to animal keepers.

Animal food products, particularly those for domesticated animals, such as dogs, cats, etc., are primarily comprised of several common ingredients. These ingredients may be present in varying amounts depending upon the targeted animal for which the food is intended. Also, several nutritional supplements and dietary additives may be included in an animal food product. The types and amounts of the ingredients and dietary supplements existing in a particular animal food product largely depends upon the animal for which the food is intended. For instance, depending upon an animals age, weight, or species, the animal food product may comprise differing compositions or amounts by weight of ingredients and/or dietary supplements. Other factors might include whether an animal is sick, or is known to possess a genetic defect or disease, or whether an animal is allergic or prone to adverse reactions to certain kinds of ingredients. Still other animal food products are designed to increase the nutritional value of the food product. This may be accomplished by various means such as providing a food product that is high in protein, low in calories, or that provides a greater number of essential vitamins and minerals, etc.

a. Common Animal Food Product Ingredients

The ingredients or nutrients found in animal food products can be divided into several subcategories. These categories, which are discussed in greater detail below, include protein, carbohydrates, fats, vitamins and minerals, and water. Several different types of these ingredients are available and one ordinarily skilled in the art will be able to recognize that several different types may be present in a particular composition depending upon the targeted animal.

Protein. Common animal food protein sources include meat, fish, and some plant ingredients. Protein has many functions in the body, but is best known for supplying amino acids, or protein subunits, to build hair, skin, nails, muscles, tendons, ligaments, and cartilage. Protein also plays a main role in hormone production. Animals, particularly dogs and felines, require essential amino acids, such as taurine for cats, that are not all found in single plant protein sources.

In addition, for a protein source they may contain poultry meal, by-product meat, meat and bone meal, or other animal or fish meal by-products. At times as well, grain protein supplements such as corn gluten, soybean meal or other oil seed meals may be added.

Carbohydrates. Common carbohydrate sources are plants and grains. Carbohydrates, also categorized as starches (sugars) and fibers, provide energy and bulk, respectively. Starches are made up of various types of sugar, such as glucose or fructose. Sugar can be easily converted by the dog or cat through digestion into usable energy.

Fiber may or may not be fermented—broken down into short-chain fatty acids—by bacteria in an animal's intestines. Highly fermentable fiber sources, such as vegetable gums, provide high amounts of short-chain fatty acids. Moderately fermentable fibers, such as beet pulp, provide short-chain fatty acids and bulk for moving waste. Slightly fermentable fibers, such as cellulose, provide mainly bulk for moving waste through the digestive tract and only a few short-chain fatty acids.

Selected fibers comprising the total dietary fiber content may comprise: *Morinda citrifolia* dietary fiber, apple pomace, barley, beet pulp, brewers rice, brown rice, carrageenan, carrots, cellulose, citrus pulp, corn, corn meal, corn grits, ground yellow corn, corn bran, dried whey, fructooligosaccharides, grain sorghum, gum arabic, gum talha, carob bean gum, guar gum, lactose, mannanoligosaccharides, molasses, oat groats, oatmeal, peanut hulls, pearled barley, peas, pea fiber, pectin, potato, psyllium, rice, rice bran, soybean hulls, sugar, tomato pomace, vegetable gum, wheat, wheat bran, and xanthan gum. However, one ordinarily skilled in the art will recognize that these are not meant to be all inclusive, but only illustrative of the types of fibers that may be included in the animal food product of the present invention.

In addition, there may typically be one or two cereal grains, generally corn, wheat and/or rice.

Fats. Fats are found in meats, fish, and plant oils, such as flax and vegetable oils. Fat, for all its bad press, fulfills many vital body functions. Animal cell membranes are made of fat. Fat is also responsible for helping maintain body temperature, controlling inflammation, and more. Fat is the primary form of stored energy in the body—providing twice as much energy as carbohydrates or proteins. Fats also provide the important fat subunits, omega-6 and omega-3 fatty acids. Omega-6 fatty acids are essential for maintenance of skin and coat and proper membrane structure. Omega-3 fatty acids have been shown to be important in blood clotting and decreasing inflammation.

Vitamins & Minerals. Vitamins are responsible for aiding functions such as bone growth, blood clotting, energy production, and oxidant protection. Vitamins A, D, E, and K require fat for absorption into the body, while vitamins such as the B-complex vitamins and vitamin C, need water to be absorbed into the body. Minerals provide skeletal support and aid in nerve transmission and muscle contractions.

Water. Water is the single most important nutrient for the body. Without it, the body cannot transport nutrients, digest nutrients for energy, regulate temperature, or eliminate waste.

As will be recognized by one ordinarily skilled in the art, specific compositions or amounts present by weight of each of these ingredients varies from product to product. However, for the most part, the percentages by weight are: Protein from 14% to 50%, usually 20% to 25%; fat from 5% to 25%; carbohydrates, where fiber is typically present in the range of from about 3% to 14%, usually about 5% to 7%; vitamins and minerals from 1% to 10%; and water or other moisture ingredients making up the remainder.

b. Recent Developments in Animal Food Products

Largely in part to research and technological advancements, animal food products have become more advanced in their ability to specifically target and cater to specific needs of different animals. The following are only intended as examples of some of the various types of animal food products and their particular problem solving capabilities that are in existence today.

EXAMPLE ONE

In one composition, ingredients are designed and included to improve several important clinical indicators in an animal suffering from renal disease. These needs are met by providing a pet food composition which improves several important clinical indicators in the renal patient and includes adequate protein, has low phosphorus levels, improves metabolic buffering, and lowers blood triglyceride levels in the animal. The animal is fed a composition comprising 17 to about 22 percent crude protein, about 13 to about 15 percent fat, about 7 to about 12 percent total dietary fiber, and fermentable fibers which have an organic matter disappearance of 15 to 60 percent when fermented by fecal bacteria for a 24 hour period, the fibers being present in amounts from about 1 to 11 weight percent of supplemental total dietary fiber. The animal is maintained on the diet for a sufficient period of time to reduce BUN and creatinine levels in the animal.

The fermentable fibers are selected from the group consisting of beet pulp, gum arabic, gum talha, psyllium, rice bran, carob bean gum, citrus pulp, pectin, fructooligosaccharides, mannanoligosaccharides and mixtures thereof. Most preferably, the fermentable fibers are beet pulp or a blend of beet pulp, gum talha or gum arabic, and fructooligosaccharides.

Optionally, the composition may also have a phosphorus content of less than about 0.50%, and preferably less than about 0.25%, by weight to prevent hyperphosphatemia. The composition may also optionally contain potassium citrate as a metabolic buffering agent. Inclusion of potassium citrate has been found to ameliorate metabolic acidosis in animals with renal disease.

EXAMPLE TWO

Pets, similar to humans, exhibit significant genetic diversity which affects their overall health and nutritional requirements. Ingredient tolerance and nutrient metabolism differ among breeds. Breed-specific dog food formulations that comprise chicken meat as the major ingredient, rice as the predominant (or sole) grain source, fruit and/or vegetable fiber as the primary or sole fiber source, unique fat and antioxidant blend, vitamins, herbs and spices, carotenoids, and no corn or artificial colors, preservatives, flavors or sugars may be provided to cater to these specific needs.

The formulations designed for specific breeds are designed based on the genetic diversity of different dog breeds. More specifically, dog food formulations are designed taking into account the different food allergies of different dog breeds.

Breed-specific dog food formulations may comprise the following unique combination of ingredients and features: (i) chicken meat and/or meal as the primary ingredient (and only meat source); (ii) rice as the primary grain source; (iii) unique antioxidant blend; (iv) unique fat blend; (v) organic minerals; (vi) unique fiber blend; (vii) specific combinations of herbs and species; (viii) no added artificial colors or preservatives, flavors or sugars; and (ix) nutrition substantiation through AAFCO feeding studies.

These pet food formulations, having the above ingredients and features, provide: (1) total digestibility ranges from 85–90%; (2) no meat products other than chicken meat and/or meal; (3) absence of any corn; (4) a blend of vitamins including tocopherols, vitamin C (ascorbic acid), minerals (copper, zinc and iron in inorganic and organic complex form), carotenoids (e.g., beta carotene and lutein), and herbs (including rosemary); (5) a fat blend including canola oil, salmon oil and evening primrose oil; (6) fruit and/or vegetable fiber rather than grains, such as tomato pomace, as the primary fiber source; (7) herbs and spices including spearmint, ginger, ginseng, ginkgo, parsley and Yucca schidigera extract; and (8) kibble size, shape, feed recommendations tailored to specific breed.

EXAMPLE THREE

Disease prevention is important both in humans as well as companion animals. A healthy immune system plays an important role both in preventing and fighting disease. Enhancing immune response and improving the overall health of companion animals, such as felines and dogs, is achievable through a pet food supplement and process which includes beneficial amounts of .beta.-carotene in the animal's diet. Some studies have reported only low to undetectable amounts of .beta.-carotene in the circulating blood and organs of dogs. Further, because of the known inability of cats to convert .beta.-carotene to vitamin A, their diets have not included beta.-carotene supplements.

The animal is fed a diet which includes from about 1 to about 50 mg/day of .beta.-carotene (from about 6 to about 315 mg .beta.-carotene/kg diet). Such a diet provides sufficient .beta.-carotene to be absorbed by the animal and supplied to the blood and blood leukocytes and neutrophils in the animal.

EXAMPLE FOUR

Obesity is the most common nutritional disease of companion pets in an affluent society. It in fact exceeds by far all deficiency diseases combined. Obesity generally is considered present when body weight of the companion pet is 15% or more greater than optimum, which is the point at which health problems begin increasing with increasing weight. It has, for example, been reported that in affluent societies from 24% to 44% of the dogs are obese. Generally speaking, the incidence of obesity in companion pets increases with the age of the pet. Similar to humans, as the animals age body fat increases, and the amount of lean body mass decreases.

A dog food composition may be provided, which contains a small, but effective amount of simmondsin component to provide a simmondsin activity within the range of about 0.1 to about 1.5 percent by weight of the composition. Weight reduction and obesity prevention is accomplished by adding pet food that contains the above-defined range of simmondsin activity, contributed by simmondsin analogues or mixtures thereof such as that synthesized or derived from jojoba seeds or defatted jojoba seed meal, to a companion pets diet on a regular and sustained basis until sufficient weight reduction occurs, and obesity occurrence or recurrence is prevented.

EXAMPLE FIVE

Large or giant breed puppies grow to a larger body size than smaller breed puppies, and as a result, they have a genetic propensity to grow very rapidly when provided with a nutrient-rich diet. However, it has been found that such rapid growth can result in an imbalance between the rate of body weight gain and skeletal growth of the puppies. In addition, the bones of large and giant breed dogs are less dense than bones of smaller breed dogs. Accordingly, large or giant breed puppies are often susceptible to skeletal growth abnormalities including disturbances in endochondral ossification which may lead to osteochondrosis, hypertrophic osteodystrophy, and hip dysplasia.

Pet food compositions may comprise from about 0.75 to 0.95 percent by weight calcium and from about 0.62 to 0.72 percent by weight phosphorus on a total weight basis. Preferably, the ratio of calcium to phosphorus is greater than about 1:1 and is preferably about 1.2:1 to 1.3:1. The composition further comprises a source of protein, a source of fiber, and a source of fat.

When the pet food composition of the present invention is fed to large or giant breed puppies on a daily basis, it has been found to be effective in reducing the incidence of skeletal disease while providing adequate growth rates.

EXAMPLE SIX

Diarrhea is defined as an increase in fecal water content with an accompanying increase in the frequency, fluidity or volume of bowel movements. Also, diarrhea is the primary clinical sign of intestinal disease in the dog and one of the most common presenting signs in veterinary medicine. Several approaches may be taken to improve the gastrointestinal diets of companion animals to address the problem.

Some compositions use reduced fiber and fat as methods to help alleviate the diarrhea. Others use high quantities of cellulose fiber to overwhelm the gastrointestinal tract with an insoluble fiber. The end product of this approach is an increase in fecal bulk.

Another method is to provide a composition that uses moderate levels of dietary fermentable fibers to provide the intestinal tract with an ample supply of preferred oxidative fuel sources. This approach seeks to relieve symptoms of chronic diarrhea by "feeding" the cells which line the gastrointestinal tract of the animal. Epithelial cells, such as enterocytes and colonocytes, depend upon respiratory fuels to maintain cellular turnover and function. These respiratory fuels can either be derived from the bowel lumen or from systemic circulation. Colonocytes derive more than 70% of their energy from lumenal nutrition supplied by short-chain fatty acids (SCFAs).

These examples and their ingredients, while illustrative of known prior art advances in animal food products, may be significantly enhanced through the inclusion of *Morinda citrifolia* as an ingredient. By doing so, these products may provide yet further advantages and benefits to the animals for which they are intended. As there exists many different types of animal food products, each containing significantly different compositions of ingredients, the present invention seeks to provide an animal food product that is capable of enhancing any specific composition or formulation by the addition of *Morinda citrifolia* dietary fiber. As such, several Examples have been provide, which are discussed below, wherein *Morinda citrifolia* dietary fiber has been added to a specific composition of ingredients to create an enhanced and beneficial animal food product.

III. *Morinda Citrifolia* Dietary Fiber Enhanced Animal Food Product

The present invention provides significant advantages over prior art animal food products due to the inclusion of *Morinda citrifolia* within the animal food product composition.

The present invention features an animal food product containing an amount or percent by weight of *Morinda citrifolia* dietary fiber as part of the total dietary fiber content in an animal food product. The *Morinda citrifolia* is added or mixed into the animal food product composition, along with the other ingredients comprised therein. As stated above, pet foods are normally classified as wet, semi-wet (or soft), and dry. These classifications largely depend upon the amount of moisture or water that is added to the pet food formulation or composition.

The following examples are given to illustrate various embodiments which have been made or may be made in accordance with the present invention and are given by way of example only. It is to be understood that the following examples are not all inclusive, comprehensive, or exhaustive of the many types of embodiments of the present invention which can be prepared in accordance with the technology as described herein.

EXAMPLE ONE

The following animal food formulation is concentrated on providing improved muscle and bone support.

| Ingredients | Percent by Weight |
| --- | --- |
| Glucosamine HCl | 5–10% |
| Cetyl Myristoleate | 1–5% |
| MSM | <1% |
| Chondroitin Sulfate | 1–5% |
| Perna Mussel Extract | 1–5% |
| water | 40–60% |
| *Morinda Citrifolia* (Noni) concentrate | 10–30% |
| flavor | <1% |

EXAMPLE TWO

The following animal food formulation is concentrated on providing improved skin and hair support.

| Ingredients | Percent by Weight |
|---|---|
| Omega-3 Fish Oil | 10–20% |
| OPC's Complex | <1% |
| Quercetin | 1–5% |
| Golden Seal Extract | 1–5% |
| Garlic Oil Extract | 5–10% |
| water | 40–60% |
| lecithin | 1–5% |
| flavor | <1% |
| *Morinda Citrifolia* (Noni) extract | 10–30% |

EXAMPLE THREE

The following animal food formulation is concentrated on providing improved immune system support.

| Ingredients | Percent by Weight |
|---|---|
| 1,3 beta D-Glucan | <1% |
| Astragalus Extract | 5–10% |
| Echinacea Extract | 1–5% |
| Japanese Mushrooms (Maitake, Shiitake, Reishi) Extract | 1–5% |
| Shark Liver Oil (squalamine) | 5–10% |
| water | 40–60% |
| flavor | <1% |
| lecithin | 1–5% |
| *Morinda Citrifolia* (Noni) extract | 10–30% |

EXAMPLE FOUR

The following animal food formulation is concentrated on providing improved digestive system support.

| Ingredients | Percent by Weight |
|---|---|
| Glutamine | 5–10% |
| Milk Thistle Extract | 5–10% |
| Ginger Extract | 1–5% |
| Licorice Extract, DGL | 1–5% |
| Tumeric Extract | 5–10% |
| flavor | <1% |
| water | 40–60% |
| *Morinda Citrifolia* (Noni) extract | 10–30% |

EXAMPLE FIVE

The following animal food formulation is concentrated on providing improved anti-aging support.

| Ingredients | Percent by Weight |
|---|---|
| OPC's Complex | 5–10% |
| Ginko Biloba Extract | 1–5% |
| Co-enzyme Q10 | 1–5% |
| Arginine | 10–20% |
| Dimethylglycine | 1–5% |
| flavor | <1% |
| water | 40–60% |
| *Morinda Citrifolia* (Noni) extract | 10–30% |

EXAMPLE SIX

The following animal food formulation is concentrated on providing improved overall health and well-being.

| Ingredients | Percent by Weight |
|---|---|
| OPC's Complex | 1–5% |
| Grass Extract (Barley, Wheat) | 5–10% |
| L-Carnitine | 10–20% |
| flavor | <1% |
| water | 40–60% |
| *Morinda Citrifolia* (Noni) extract | 10–30% |

As stated, these examples are not intended to be limiting in any way. One ordinarily skilled in the art will recognize the many different compositions of ingredients that may be incorporated into an animal food product. Moreover, one ordinarily skilled in the art should recognize that other ingredients may be added, that are not listed here, and included with the *Morinda citrifolia* dietary fiber to complete the pet food formulation or composition. This especially becomes evident when one considers the many different types of pet food formulations existing in the market today, including those that are capable of targeting a specific need of a companion animal or a particular companion animal altogether. As such, the concentration or percent by weight of the *Morinda citrifolia* dietary fiber, as well as any of the other ingredients, may be increased or decreased as needed.

In an alternative embodiment, the *Morinda citrifolia* dietary fiber may be contained in various other animal food products, such as pet food snack, biscuits, etc.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed is:

1. An animal food product comprising:
    a combination of ingredients designed to provide predetermined, animal-specific and animal need-specific nutrition, wherein said ingredients comprise:
    *Morinda citrifolia* dried juiceless fruit fiber; and
    at least one of:
        (i) a protein;
        (ii) a fat;
        (iii) a vitamin;
        (iv) a mineral; and
        (v) water.

2. The animal food product of claim 1, wherein the protein comprises at least one of:
    (i) a poultry meal;
    (ii) by-product meat;
    (iii) meat and bone meal;
    (iv) an animal meal by-product; and
    (v) a grain protein.

3. The animal food product of claim of claim 1, further comprising at least one of: apple pomace; barley; beet pulp; brewers rice; brown rice; carrageenan; a carrot; cellulose; citrus pulp; corn; corn meal; corn grits; ground yellow corn; corn bran; whey; a fructooligosaccharide; grain sorghum; gum arabic; gum talha; carob bean gum; guar gum; lactose; a mannanoligosaccharide; molasses; an oat groat; oatmeal; a peanut hull; barley; a pea; pea fiber; pectin; a potato; psyllium; rice; rice bran; a soybean hull; sugar; tomato pomace; vegetable gum; wheat; wheat bran; and xanthan gum.

4. The animal food product of claim 1, wherein the fat comprises at least one of:
   (i) flax; and
   (ii) vegetable oil.

5. The animal food product of claim 1, wherein the water is present in an amount between about 20–80 percent by weight.

6. The animal food product of claim 1, further comprising glucosamme HCI present in an amount between about 5–10 percent by weight.

7. The animal food product of claim 1, further comprising cetyl myristoleate present in an amount between about 1–5 percent by weight.

8. The animal food product of claim 1, further comprising MSM present in an amount between about 0.01–1 percent by weight.

9. The animal food product of claim 1, further comprising chondroitin sulfate present in an amount between about 1–5 percent by weight.

10. The animal food product of claim 1, further comprising perna mussel extract present in an amount between about 1–5 percent by weight.

11. The animal food product of claim 1, further comprising a flavor agent present in an amount between about 0.01–1 percent by weight.

12. The animal food product of claim 1, further comprising omega-3 fish oil present in an amount between about 10–20 percent by weight.

13. The animal food product of claim 1, further comprising OPC's complex present in an amount between about 0.01–1 percent by weight.

14. The animal food product of claim 1, further comprising quercetin present in an amount between about 1–5 percent by weight.

15. The animal food product of claim 1, further comprising golden seal extract present in an amount between about 1–5 percent by weight.

16. The animal food product of claim 1, further comprising garlic oil extract present in an amount between about 5–10 percent by weight.

17. The animal food product of claim 1, further comprising lecithin present in an amount between about 1–5 percent by weight.

18. The animal food product of claim 1, further comprising 1,3 Beta D-glucan present in an amount between about 0.01–1 percent by weight.

19. The animal food product of claim 1, further comprising astragalus extract present in an amount between about 5–10 percent by weight.

20. The animal food product of claim 1, further comprising echinacea extract present in an amount between about 1–5 percent by weight.

21. The animal food product of claim 1, further comprising japanese mushrooms extract present in an amount between about 1–5 percent by weight.

22. The animal food product of claim 1, further comprising shark liver oil present in an amount between about 5–10 percent by weight.

23. The animal food product of claim 1, further comprising glutamine present in an amount between about 5–10 percent by weight.

24. The animal food product of claim 1, further comprising milk thistle extract present in an amount between about 5–10 percent by weight.

25. The animal food product of claim 1, further comprising ginger extract present in an amount between about 1–5 percent by weight.

26. The animal food product of claim 1, further comprising licorice extract present in an amount between about 1–5 percent by weight.

27. The animal food product of claim 1, further comprising tumeric extract present in an amount between about 5–10 percent by weight.

28. The animal food product of claim 1, further comprising OPC's complex present in an amount between about 5–10 percent by weight.

29. The animal food product of claim 1, further comprising gingko bilboa extract present in an amount between about 1–5 percent by weight.

30. The animal food product of claim 1, further comprising co-enzyme Q10 present in an amount between about 1–5 percent by weight.

31. The animal food product of claim 1, further comprising arginine present in an amount between about 10–20 percent by weight.

32. The animal food product of claim 1, further comprising dimethylglycine present in an amount between about 1–5 percent by weight.

33. The animal food product of claim 1, further comprising OPC's complex present in an amount between about 1–5 percent by weight.

34. The animal food product of claim 1, further comprising alfalfa grass extract present in an amount between about 5–10 percent by weight.

35. The animal food product of claim 1, further comprising L-carnitine present in an amount between about 10–20 percent by weight.

* * * * *